US00PP33572P2

(12) United States Plant Patent
Egger

(10) Patent No.: US PP33,572 P2
(45) Date of Patent: Oct. 19, 2021

(54) ***HEUCHERA* PLANT NAMED 'RUBY TUESDAY'**

(50) Latin Name: ***Heuchera* hybrid**
Varietal Denomination: Ruby Tuesday

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/212,170

(22) Filed: Mar. 25, 2021

(51) Int. Cl.
*A01H 6/80* (2018.01)
*A01H 5/02* (2018.01)

(52) U.S. Cl.
USPC ..... Plt./440

(58) Field of Classification Search
USPC ..... Plt./440
See application file for complete search history.

*Primary Examiner* — Annette H Para
(74) *Attorney, Agent, or Firm* — Klarquist Sparkman, LLP

(57) ABSTRACT

A new and distinct *Heuchera* plant characterized by medium, veiled, ruffled, red to bronze-green leaves, a medium plant size, showy light pink flowers in spring through summer, and excellent vigor.

2 Drawing Sheets

Botanical denomination: *Heuchera* hybrid.
Variety designation: 'Ruby Tuesday'.

BACKGROUND OF THE INVENTION

The present invention relates to a new and distinct cultivar of *Heuchera* and given the cultivar name of 'Ruby Tuesday'. *Heuchera* is in the family Saxifragaceae. *Heuchera* 'Ruby Tuesday' originated from a cross of proprietary, unreleased plants. Compared to *Heuchera* 'Marmalade' (U.S. Plant Pat. No. 15,945), the new cultivar has a smaller habit, smaller leaves that are veiled rather than unveiled and larger flowers that are pale pink rather than green-white.

Compared to *Heuchera* 'Lime Rickey' (U.S. Plant Pat. No. 16,210), the new cultivar has larger leaves which are veiled, a larger, rounder habit and larger flowers.

This new *Heuchera* is distinguished by:

1. medium, veiled, ruffled, red to bronze-green leaves,
2. medium plant size,
3. showy pale pink flowers spring into summer, and
4. excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
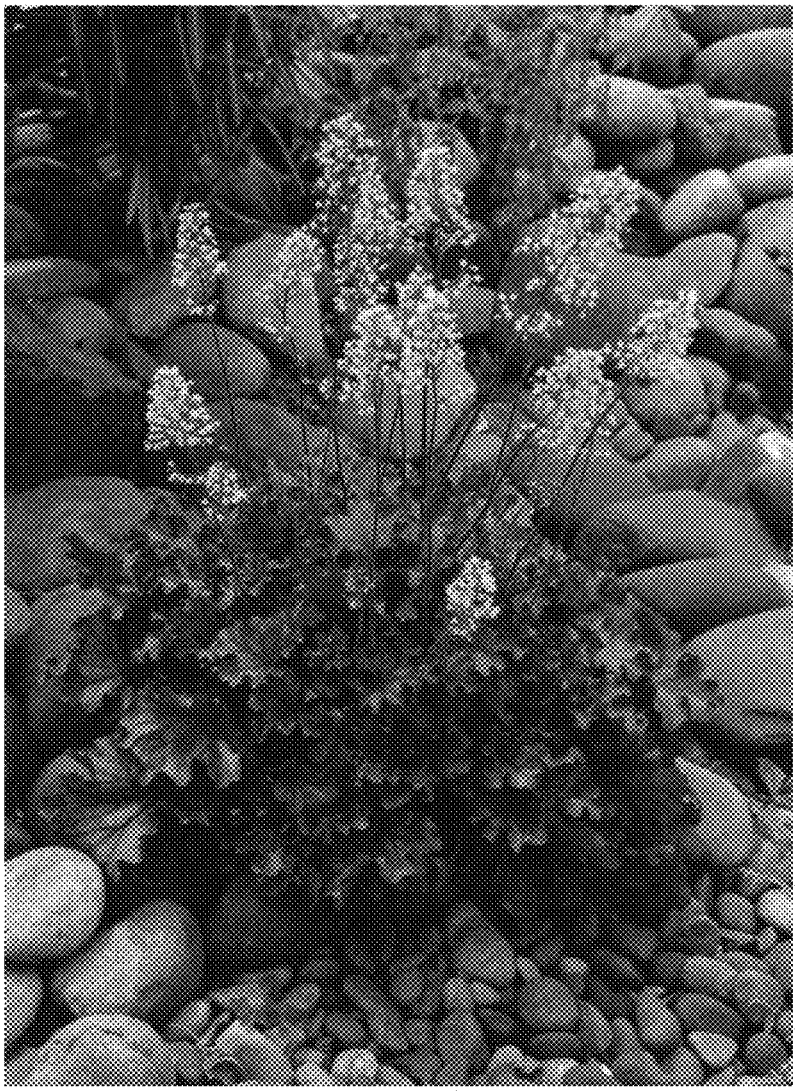
FIG. 1 shows a 10 month-old *Heuchera* 'Ruby Tuesday' in a garden setting in Canby, Oreg.
Figure 2:
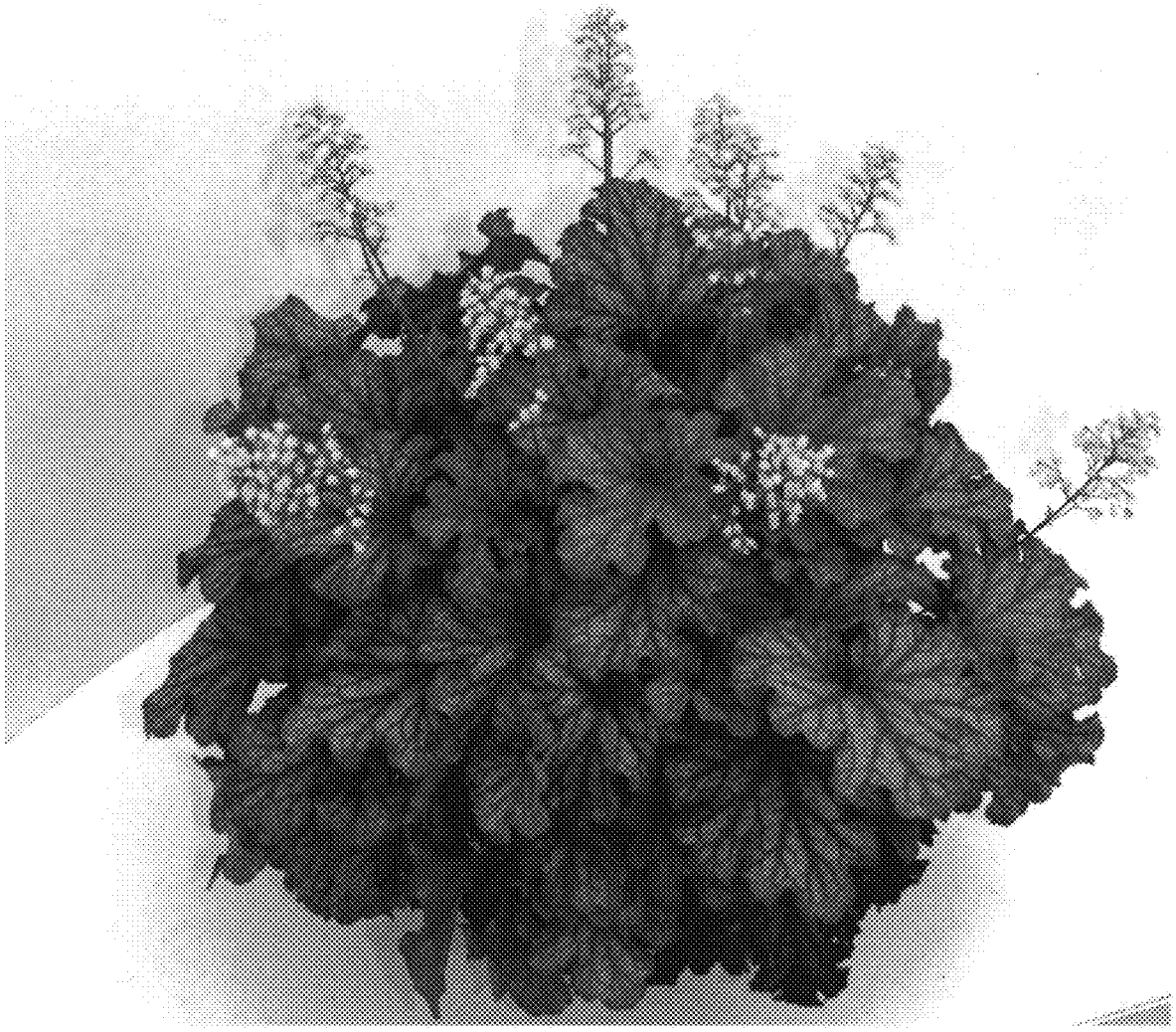
FIG. 2 shows a group of 12 month-old *Heuchera* 'Ruby Tuesday' in flower, greenhouse grown in a 1 gallon container.

The following is a detailed description of the new *Heuchera* cultivar based on observations of 9 month-old specimens grown in the ground in the trial bed in shade in October in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5$^{th}$ edition, 2007.

Plant:

*Form*.—Basal rosette, herbaceous perennial.
*Hardiness*.—USDA Zone 4 to 9.
*Size*.—22 cm tall from top of the foliage to the ground and 36 cm wide.
*Habit*.—Mound.
*Vigor*.—Excellent.
*Roots*.—Fibrous, freely branching, fine, and white in color; roots develop easily from stem cuttings.

Leaf:

*Type*.—Simple.
*Arrangement*.—Basal.
*Shape*.—Broadly ovate.
*Lobing/division*.—5 main lobes, with 2 to 3 shallow secondary lobes.
*Venation*.—Palmate, veins topside young foliage, N34A, bottom side Red 47A, older foliage, top side Greyed Green 191A, bottom side, 194B.
*Margins*.—Crenate and undulate.
*Apex*.—Mucronulate.
*Base*.—Cordate, lobes overlapping at the base.
*Blade size*.—Grows to 8.5 cm long and 9.5 cm wide.
*Surface texture*.—Both sides glandular.

*Petiole description*.—Grows to 11.5 cm long and 2.5 mm wide, glandular, background, Yellow Green 152C, with sparse stippling 187C.

*Leaf color*.—Spring new growth topside 179A, with a white veil of N155C, bottom side Greyed Purple 183C; summer and winter topside Green N137A with the veil Greyed Green 193C, bottom side closest to Greyed Red 178A.

Inflorescence:

*Size*.—Grows to 7 cm wide and 17 cm long.

*Type*.—Thyrse.

*Number of flowers per thyrse*.—85 to 100 per thyrse.

*Number of thyrse*.—About 33 in spring bloom.

*Peduncle*.—Grows to 47 cm tall, 3 mm wide at base, Greyed Purple 186A at base blending to Greyed Purple 185A, glandular hairs, with 1 to 4 petiolate leaves (ovate, blades grow to 4.7 cm long and 3.5 cm wide, 3 lobed, margin biserrate, color the same as the leaves).

*Pedicel*.—1 to 4 mm long, with glandular hairs, Greyed Purple 185A.

*Bloom period*.—May to October in Canby, Oreg.

Flower bud:

*Size*.—2.5 mm wide and 4 mm long.

*Description*.—Glandular puberulent, ovoid.

*Color*.—Top half White N155D, bottom half Greyed Purple 186D.

Flower:

*Type*.—Perfect.

*Shape*.—Campanulate.

*Size*.—5 mm long and 4.5 mm wide.

*Petal description*.—5 in number, 3 mm long and 1 mm wide, reflexed, tip acute, margin entire, glabrous on top and bottom sides, sometimes glandular, White NN155D on both sides.

*Calyx description*.—4 mm long and 4 mm wide, with 5 lobes, divided 1/2 way to the base, glandular hairs on outside, glabrous inside, tip obtuse, margin entire, both sides top half White N155D, bottom half White N155C.

*Stamen description*.—5 in number, each 3.5 mm long, White NN155C, anthers Yellow Orange 21C, pollen, Yellow-Orange 22A.

*Pistil description*.—One central two beaked pistil, 4 mm long, ovary 1 mm long and Green Yellow 2D, style 3 mm long , White NN155B.

*Fragrance*.—None.

*Lastingness*.—Each thyrse blooms for about 2 weeks on the plant.

Fruit:

*Type*.—Two-beaked ovoid capsule.

*Fertility*.—Low.

*Color*.—Greyed Brown 199C.

Seed:

*Shape*.—Linear.

*Size*.—2 mm long.

*Color*.—Black 203B.

Disease and pest tolerance: Pest and disease resistance are typical for this type of *Heuchera*. No known resistances.

I claim:

1. A new and distinct *Heuchera* plant as herein illustrated and described.

* * * * *